United States Patent [19]

Bires et al.

[11] Patent Number: 4,848,377
[45] Date of Patent: * Jul. 18, 1989

[54] ARTICLE FOR PERMANENT STRUCTURE ALTERATION OF HAIR

[75] Inventors: Carmen D. Bires, Long Valley; Michael W. Helioff, Westfield; Ratan K. Chaudhuri, Butler, all of N.J.

[73] Assignee: GAF Corporation, Wayne, N.J.

[*] Notice: The portion of the term of this patent subsequent to Dec. 27, 2005 has been disclaimed.

[21] Appl. No.: 105,783

[22] Filed: Oct. 8, 1987

[51] Int. Cl.$^4$ .............................................. A45D 2/00
[52] U.S. Cl. .................................. 132/222; 132/221; 132/207; 424/71
[58] Field of Search ............... 132/221, 222, 202, 203, 132/204, 207, 210; 424/71, 72

[56] References Cited

U.S. PATENT DOCUMENTS

| | | | |
|---|---|---|---|
| 4,206,196 | 6/1980 | Davis | 132/202 |
| 4,403,622 | 9/1983 | Stahl | 132/7 |
| 4,605,021 | 8/1986 | Hodson et al. | 132/33 R |
| 4,632,132 | 12/1986 | Bustance et al. | 132/7 |
| 4,793,994 | 12/1988 | Helioff et al. | 424/71 |

Primary Examiner—Gene Mancene
Assistant Examiner—Adriene J. Lepiane
Attorney, Agent, or Firm—Marilyn J. Maue; Joshua J. Ward

[57] ABSTRACT

An article of manufacture comprising an absorbent hair wrapping material coated or impregnated with a hair structure altering, water soluble solution and the process of employing the wrapping. The hair wrapping material is capable of retaining between about 5 and about 15 times its weight of water and a water soluble hair reducing lotion. The water soluble hair reducing lotion contains one of an N—$C_8$ to $C_{22}$ alkyl lactam conditioner or an N— quaternized amino lactam.

17 Claims, No Drawings

ARTICLE FOR PERMANENT STRUCTURE ALTERATION OF HAIR

In one aspect this invention relates to a novel article of manufacture for use in permanent waving or permanent straightening of hair.

In another aspect the invention relates to a method of utilizing said article of manufacture and in still another aspect the invention relates to a method of producing the article of manufacture.

BACKGROUND OF THE INVENTION

The general procedure and reducing lotions employed in the curling or straightening of hair are well known and typically involve steps of wetting the hair, uniformly applying the reducing lotion, wrapping the ends of the lotion saturated hair on rods, remoistening the wrapped hair, positioning a strip of absorbent material around the hair line to absorb drippings, allowing the lotion to set hair in a restructured form within a determined period and then neutralizing to halt the chemical action. It is evident that the above procedure has many chemical and phsyical disadvantages including a time consuming, messy procedure, the use of liquid lotions, often in breakable containers, prolonged exposure of sensitive skin to the chemical action of the lotion and danger of lotion run-off in the eyes and facial skin of the subject.

A particularly serious problem exists with the use of alkaline permanent reducing solutions, since the skin is made up of soft keratin which is more easily broken down than the hard keratin of hair. Entry of the solution into any abrasion on the scalp often causes severe dermatitis and scalp inflammation. These solutions also cause serious damage to the cornea if accidentally dripped or splashed into the eye. Another danger is to the professional practitioner whose nails and finger skin softens and discolors due to continued use. Although gloves offer protection, they cause sweating of the hands and interfere with movements of the finger; thus, many operators do not use them.

The art has long sought means and possibilities to overcome the above disadvantages whereby hair waving and straightening solutions are rendered less damaging to the skin and hair and methods whereby the solutions are easier, faster and simpler to apply or use while achieving the same or more effective results for heat or cold, professional or home permanent waving and hair straightening.

Accordingly, it is an object of the present invention to overcome all of the above difficulties and to provide a process for altering the structure of hair with a novel structure reforming material which enables shorter processing time.

Another object of the invention is to provide a hair reducing material which promotes a higher degree of curl in a shorter period of time.

Another object of this invention is to eliminate drip and run-off of processing lotion during the permanent waving or straightening of hair.

Another object is to provide a product of manufacture capable of altering hair structure which has superior properties and which can be produced in a commercially advantageous form.

These and other objects will become apparent from the following description and disclosure.

THE INVENTION

In accordance with this invention there is provided flexible hair wrapping material capable of absorbing and retaining between about 5 and about 15 times its weight of water, preferably between about 7 and about 12 times its weight of water, which is coated or impregnated with from about 3 to about 130 grams per square meter of a water soluble, hair structure altering solution.

The absorbent wrapping employed in the present invention is a porous, flexible material, resistant to shredding and tear and having the ability to retain the liquid hair treating formulation in a water releasable form. Such materials include pads, swatches or rollers composed of paper, woven or non-woven material in the form of a fabric, plastic, felt, sponge, gauze, or blotter which includes both mono- and poly-ply laminated materials such as the laminations employed for diapers, etc. Also, the material may have a relatively smooth surface or be crimped or creped to attain additional absorbent properties. Particularly suitable is microsponge, preferably closed pore non-retriculated sponge having from about 5 to about 150 pores/inch, most preferably from about 40 to about 120 pores/inch.

The coated wrapping material can be used in a wet or dry state and can be coated or impregnated on one or both sides of its surface or be completely saturated with a suitable hair altering solution gel or paste, as described in U.S. Pat. No. 4,206,196, incorporated herein by reference.

The hair can be wetted by prerinsing or shampooing or the impregnated absorbent wrapping can be applied directly on dry hair wound rods or preferably used to wrap the hair in a straightened condition before winding on rods for softening and relaxation of the hair fiber. The softening effect is produced by rupture of the disulfide bonds of the cystine residue in the keratin protein to produce the corresponding cysteine residue. However, the present wrapping can also be disposed in the form of a winding rod, e.g., as a tubular spongy material impregnated with the waving lotion. Further, such sponge rollers may be secured in rolled position by including on their surface a plurality of interlocking filaments. Such a filamented surface eliminates crimping of the curl normally associated with conventional rods having separate fasteners. However, it is to be understood that conventional winding rods composed of plastic or other material resistant to the reducing and neutralizing lotions also can be employed. Such rods can be equipped with individual clamp fasteners or are so constructed as to have interlocking means or lips or Velcro-like surfaces for engaging and securing one rod to another.

In the relaxed state the hair fiber, is held at room temperature, or slightly increased temperature up to about 50° C. for acceleration of the chemical reaction, for a period of between about 5 and about 20 minutes; after which the hair is water washed to remove the reducing formulation and the disulfide bonds are reformed by air oxidation or by the application of an oxidizing lotion which sets the hair according to the desired structure. The degree of curl depends primarily on the size and shape of the rods or the thickness of the wrapping on which the hair is wound and processing time.

Generally, the wrapping employed in the present invention for securing hair sections before winding on rods has a thickness of from about 1/32 to about ¼ inch depending on the tightness of the curl desired and the size of the rod. However, when the rods are composed of said wrapping, any thickness compatable with the desired curl can be employed. For hair straightening wrappers of 1-2 inch thickness can be employed. In such hair straightening processes, the use of a spongy material for wrapping grips the hair strands and supplies the tension needed to hold strands in a straightened position.

The hair altering solutions or lotions of the present invention include any of the conventional permanent waving or straightening formulations. As the term "lotion" is used herein, it is to be understood that this term includes a cream, a gel, an emulsion or a watery liquid.

The activity or effectiveness of hair shaping preparations is based mainly on the inclusion therein of an agent for softening and relaxing the keratin protein present in hair by reducing the disulfide linkages of keratin. The hair fiber is wound on rods to achieve the desired waving effect or manipulated into a straightened condition and allowed to remain wetted with the reducing lotion for a desired period, after which the reducing lotion is rinsed off and finally oxidized with a neutralizing solution or air oxidized.

Basically, hair is softened and swelled by rupture of disulfide bonds present in the cystine component of keratin by the use of an alkaline reducing agent. Cleavage of at least some of the disulfide bonding to form the corresponding cystine residue is necessary to allow for molecular rearrangement which takes place during the hair fiber molding operation. The reductive fission of hair disulfides generally causes reddening of the scalp area and damage to the hair fiber, particularly hair which has been bleached, tinted or otherwise damaged. Current hair structure altering lotions which provide relaxation of imposed stress include aqueous solutions of alkaline mercapto compounds, sulfites or bisulfites at a pH of between 7 and 9.5. In order to obtain a permanent effect, particularly in hair straightening, it is often necessary to introduce the active agent in relatively high concentration with the result that the reducing lotion is provided at almost the limit of its physiological compatability or tolerability.

Damage to hair is increased where heat waving, as opposed to cold waving, is employed. Of the reducing agents currently in use, the thioglycolates or thioglycolic acid, dithioglycolic acid and mercapto compounds such as ammonium thioglycolate, glyceryl, monothiglycolate, mercapto propionic acid and mercapto ethyl amine are most often employed in professional waving or hair straightening. Alkaline sulfites and bisulfites are gennerally reserved for home permanent use. In addition to the reducing agent, alkalis having a dissociation constant less than $5 \times 10^{-13}$, are also used to facilitate diffusion through the hair. These promoters include ammonia, ammonium hydroxide, ethanol amine, diisopropanol amine, glycine, and lysine.

All of the above reducing lotions cause some degree of hair damage depending on the tightness and thickness of the curl, the length of time the solution remains on the hair and the condition of the hair.

Present methods of hair structure alteration are objectionable for the reason that relatively large amounts of the reducing liquid must be applied and reapplied to assure uniform coverage and chemical action. To minimize dripping or running of reducing liquid in the eye or other facial areas of the subject it is necessary to place absorbent strips around the hairline; however even with this precaution, some dripping and running occurs causing skin irritation. Irritation resulting from routine exposure of the materials used by professional hair dresser and erythema on the scalp and neck of the subject caused by such materials are not remedied by hairline abosrbent materials which quickly become saturated. The above damaging effects on skin and hair have been mitigated by the use of several modifiers in the formulation, the best of which are disclosed in copending U.S. patent applications Ser. No. 13,617, filed Feb. 12, 1987 now U.S. Pat. No. 793,994, issued Dec. 27, 1988 and Ser. No. 60,285, filed June 10, 1987, both entitled "COMPOSITIONS USED IN PERMANENT STRUCTURE ALTERING OF HAIR", incorporated herein by reference.

Typically, hair waving preparations comprise a reducing lotion and an oxidizing lotion; although some preparations are formulated such that the oxidizing or neutralizing lotion can be omitted. Most home perm and milder waving lotions can simply be washed off the hair fiber by rinsing with water and are therefore categorized as self-neutralizing.

Generally, the hair waving or straightening lotion contains a reducing agent which is exemplified by the most commonly used ammonium thioglycolate in a solution having a pH of between about 7 and 10.5, preferably between about 8.5 and about 9.5. Other reducing agents which have found commercial use include glyceryl monothioglycolate employed at a pH of less than 7, thioglycolic acid, dithioglycolic acid, mercaptoethyl amine, mercaptropropionic acid, dithioglycolate and alkali sulfites or bisulfites. The sulfite and bisulfite reducing agents are more commonly employed for home permanents and produce a milder, softer wave. The rate of reaction of these reducing agents increases with pH and temperature, although most are applied at between room temperature and 35° C. for a period of from about 3 to about 15 minutes. The concentration of reducing agent in the aqeuous reducing lotion can vary between about 2 and about 20%. Within this range, lower concentrations are employed for damaged or bleached hair whereas for virgin, undamaged hair a concentration in the upper portion of the range can be applied.

The reducing lotion is generally employed with an alkali having a dissociation constant less than $5 \times 10^{-3}$. Suitable compounds for alkalization include ammonia, ammnonium hydroxide, sodium hydroxide, ethanol amine, diisopropanol amine, an alkali metal salt of an amino acid, e.g. glycine or lysine and guanidine. Alkali in a concentration of between about 0.5 and about 6% or 0.7-1.3 grams of free ammonia per 100 milliliters of solution is normally used.

The reducing lotion may also include a buffer such as ammonium bicarbonate to maintain a desired pH. Other additives which may be employed include catalysts for self-neutralizing permanent wave lotions, opacifiers to promote creamy appearance and fragrance to mask the odor of ammonia and thiol. Fatty acid polypeptide condensates, oxyethylated fatty alcohols and oxyethylated alkyl phenols have been employed as conditioners and emollients to minimize hair damage.

Some typical reducing hair waving lotions are illustrated by the following formulations.

| SINGLE STEP WAVING FORMULATION ||
|---|---|
| Ingredients | % By Weight |
| Ammonium thioglycolate | 0.20 |

-continued

| | |
|---|---|
| Potassium sulfite | 0.80 |
| Tartaric acid | 0.03 |
| Ethyl alcohol | 1.00 |
| Monoethanolamine | 0.03 |
| Potassium iodide | 0.60 |
| Water | 97.34 |

BISULFITE WAVING FORMULATION

| Ingredients | % By Weight |
|---|---|
| Water | 55.55 |
| Ammonium bisulfite | 22.00 |
| Hydroxyethyl cellulose | 2.50 |
| Urea | 10.00 |
| Isopropyl alcohol | 5.00 |
| Disodium phosphate | 1.14 |
| Citric acid | 0.46 |
| Ammonium hydroxide | 1.10 |
| Chelating agent | 0.05 |
| Fragrance | 0.20 |
| Surfactant | 2.00 | and

| Ingredients | % By Weight |
|---|---|
| Sodium bisulfite | 6.46 |
| Sodium borate | 4.10 |
| Sodium carbonate | 4.10 |
| Monoethanolamine | 4.92 |
| Diethanolamine | 4.92 |
| Wetting agent | 1.00 |
| Water q.s. to | 100.00 |

The basic technical premise underlying permanent hair straightening is similar to that in waving. Hair is softened, maintained straight under tension or on large rollers, e.g. 1–4 inches in diameter, for a period of time and after rinsing, rehardened by application of the neutralizer. Many hair-straightening compositions are merely thickened versions of permanent-waving products. For exampe, alkaline thioglycolate (6–8%) is formulated into a thick oil-water emulsion or cream using generous concentrations of cetyl and stearyl alcohols and high molecular weight polyethylene glycol together with a fatty alcohol sulfate as emulsifier which offers an added advantage of ready rinsability. Mixtures of ammonium bisulfite and urea have also found application in hair-straightening. Processing time may be between about 30 minutes and 2 hours, depending on the initial curliness of the hair. Conventional oxidizing neutralizers e.g. $H_2O_2$, bromates, and perborates are most often used in the final step of the process. The reformation of the cystine cross-linkages in bisulfite-reduced hair is effected by a rinse (pH 8–10).

An important class of permanent straighteners in frequent use is based on alkali as an active ingredient. Sodium or potassium hydroxide or sodium carbonate in combination with guanidine are used at concentrations of 1.5–3% in a heavy cream base. Although the recommended treatment time is only 5–20 minutes for this mixture, the straightening effect, in general, surpass those obtained with either thioglycolates or bisulfites because of the greater agressiveness of the alkaline relaxers. It has been found that a 15-minute treatment irreversibly decreases the cystine content of hair to about two thirds of its initial value.

The damaging action of strong alkali on hair is not restricted to the disulfide bonds alone. Apart from the potential of the main-chain scission, the very nature of the high pH base leads to a build-up of negative charges in hair which results in increased swelling, the latter being intensified by concurrent breakdown of the disulfide bonds.

Typical formulations for hair straightening preparations include the following Examples A-D

| | Ingredients | % By Weight |
|---|---|---|
| A | Petrolatum | 76.75 |
| | Polyoxyethylene oleyl ether | 21.00 |
| | Lactic acid, 90% | 2.20 |
| | Thymolphthalein | 0.05 |
| B | Water | 42.25 |
| | Sodium hydroxide | 2.20 |
| | Sodium lauryl ether sulfate | 6.00 |
| | Hydrolyzed animal protein | 1.00 |
| | Mineral oil | 21.30 |
| | Petrolatum | 8.00 |
| | Squalene | 3.00 |
| | Lauryl alcohol | 1.25 |
| | Lanolin fatty acids | 2.00 |
| | Cetyl alcohol | 12.00 |
| | Sodium isostearoyl-2-lactylate | 1.00 |
| C | Emulsifying wax NF (Polawax) | 7.5 |
| | Cetyl alcohol (Crodacol C-95) | 1.0 |
| | Petrolatum (Protopet) | 4.0 |
| | Carnation mineral oil | 15.0 |
| | Steareth 2 (Volpo S-2) | 0.5 |
| | DEA-oleth-10 phosphate (Crodafos N10N) | 1.5 |
| | Propylene glycol | 2.0 |
| | Steareth 10 (Volpo S-10) | 2.5 |
| | Deionized water | 53.0 |
| | Diazolidinyl urea (and) methylparaben (and) propylparaben (and) propylene glycol (Germaben II) | 1.0 |
| D i | Carbomer 941 (Carbopol 941) | 2.0 |
| | Deionized water | 77.8 |
| | Triethanolamine | 1.0 |
| ii | Ammonium thioglycolate | 13.2 |
| | Ammonia | 3.5 |
| | Laureth-23 (Emthox 5964) | 0.5 |
| | Quaternium-33 (and) ethyl hexanediol (Lanoquat 1756) | 2.0 |

Solutions (i) and (ii) are combined.

Reformation of the cystine residue by oxidation is considerably high, for example up to 90% reformation. Thus, the oxidizing solution which neutralizes the reducing agent can be regarded as a fixing lotion. Suitable oxidizing agents include hydrogen peroxide, potassium bromate, sodium bromate, sodium perborate, potassium percarbonate and, for the removal of sulfite or bisulfite reducing agents, 8 to 12% of barium chloride or calcium chloride has been used effectively. Other oxidizing agents are employed in 1 to 20% solutions in water; although hydrogen peroxide is usually employed as a 1 to 2% aqueous solution.

Typical oxidizing and neutralizing formulations for permanent waving or straightening lotions include the following.

HEAT HAIR WAVE NEUTRALIZING SOLUTION

| | Wt. % |
|---|---|
| Hydrogen peroxide | 1.3000 |
| Citric acid | 0.5000 |
| Phosphoric acid, adjusted to pH 2.84 | 0.0064 |
| Water q.s. to | 100.0000 |

NEUTRALIZER WITH CITRATE BUFFER

| | Wt. % |
|---|---|
| Hydrogen peroxide, 35% sol. | 5.00 |
| Isostearamidopropylmorpholine lactate | 0.75 |
| Cetearyl alcohol/ceteth 20 | 0.50 |
| Mineral oil | 0.07 |
| Methylparaben | 0.10 |
| Phenacetin | 0.10 |
| Fragrance | 0.05 |
| Citric acid | 4.00 |

-continued

| | |
|---|---|
| Water q.s. to | 100.00 |
| Sodium citrate q.s. to pH | 1.9 |

COLD WAVE NEUTRALIZER
WITH KERATIN HYDROLYZATE

| | Wt. % |
|---|---|
| Sodium bromate | 5.0 |
| Amphoteric surfactant | 0.5 |
| Cationic cellulosic | 0.5 |
| Perfume | 0.1 |
| Keratin hydrolyzate | 2.0 |
| Water q.s. to | 100.0 |

The reducing lotions used for coating or saturating the absorbent wrappings of the present invention can be employed in full strength which usually comprises between about 85 and about 98% aqueous solutions prefreably between about 90 and about 95% aqueous solutions of deionized water containing active reducing agent; although for hair straightening more concentrated solutions of the reducing agent up to about 20% reducer can be employed depending on the natural curl of the hair and the degree of straightening required.

The processes for coating or impregnating the hair wrappings of the present invention are achieved by inexpensive simple techniques. For example, the wrapping material, in the form of individual swatches or in the form of a sheet to be subsequently cut to a desired shape and size can be immersed in the hair altering solution until saturated and allowed to drain off liquid excess. The product can then be packaged in a damp state or may be subjected to a further step of drying and packaged as dry product. Alternatively, the wrapping material can be coated wth a spatula and doctor blade, on one or both surfaces, optionally dried and then packaged in a moisture proof container. The latter procedure is particularly useful for gel, cream or pasty hair straightening lotions. If desired, several coatings of the solution can be applied to the surface of the wrapping by the above or other coating procedures well known in the art.

Still another process of coating or impregnating the wrapping involves simply packaging a roll of the dry wrapping in the form of a continuous tape, which upon use is cut to size and then immersed in the reducing lotion. Another embodiment comprises positioning more the roll of dry wrapping tape in a dispenser equipped with a liquid reservoir for holding the reducing lotion through which the tape is passed, a squeegee device or a nipped outlet situated after the immersion bath to remove excess lotion from the saturated tape and finally a cutting or perforating device to enable separation of swatches of predetermined length. Any of the above techniques or other means of coating can be used to apply reducing lotion to a monoply wrapping sponge, gauze or between or on the plies of a multiply material composed of paper, plastic, felt or microsponge.

As indicated above, the coated or impregnated wrapping can be applied to the hair by several methods. For example, the ends of the hair can be wrapped with the impregnated material and roled on permanent waving or straightening rods in the configuration desired. As an alternative, the hair may be wound on the rods and the impregnated wrapping in the form of a cap or individual wrapping swatches can then be placed over the entire rolled area or over the hair wound on each individual rod. When employed in the dry or slightly damp state, the area in which wrappings are used is then subjected to moistening with water applied by a mist spray or any other convenient wetting device to saturate the wrapping, after which a plastic cap is placed over the scalp and the solution allowed to develop over a period of time consistent with the amount of curl required, e.g., for a period of from about 5 to about 30 minutes.

Another method involves water misting under or through perforations in the plastic cap to maintain a uniformly high moisture content during processing. The water activator can also contain a small amount of hair conditioner, e.g., between about 0.01 and about 7 wt. % of a N—$C_8$ to $C_{22}$ alkyl containing lactam including those disclosed in copending applications, Ser. Nos. 13,617 and 60,285, incorporated herein by reference. The use of a hair drier accelerates processing so that after wrapping and moistening as little as 3 minutes may be employed to complete the reducing process.

Generally, use of the present impregnated wrapping material markedly reduces the time for achieving desired structure alteration since it eliminates mixing from bottles and daubing each individual rod with lotion and provides for a more uniform distribution of lotion on the hair. Additionally, the reducing formulation contained in the wrapping minimizes exposure of the scalp to direct contact with irritating lotion and prevents dripping. It is also noted that objectionable thioglycolate odor is significantly reduced and that crimping at the hair ends is eliminated.

The reduction in processing time minimizes skin reddening and sensitivity. Also, by eliminating the premixing of permanent hair altering solutions and application of the solution directly on the hair from the formulated liquid, as was formerly required, the exposure of the operator on repeated use of these liquids or lotions is minimized. Accordingly, protective gloves normally used in the application can also be eliminated when using dry wrappers. Another advantage of the present process is that misting of the hair, as opposed to saturation to run off, permitted by the precoated or impregnated wrapping material, minimizes the danger of dripping, running and accidental splashing of the liquid onto the facial and neck area of the subject.

Still another advantage of the present invention is the elimination of solution wastage since wrappers are used only as needed. Normally, the hair altering solutions are pre-packaged in breakable bottles which contain more than an adequate amount to process the hair of the average patron. Once the bottles are unsealed, the contents cannot be stored for subsequent use since the chemicals in their diluted aqueous solutions are degradable. In the present invention, when using the dry wrapping or wrapping moistened with a concentrate reducing formulation, the chemicals are not activated until contacted with water during the wetting or misting process. Yet another advantage of the present process is that more durable curls can be achieved with larger rods or rollers, thus causing less hair damage due to breakage. Additionally, for hair straightening, very large rollers can be employed to supply tension in the straightening process. For body waves, rods of large diameter can be selectively positioned to provide curl in certain areas.

Having thus generally described the invention, reference is now had to the following Examples which illustrate preferred embodiments of the invention but which should not be construed as limiting the scope there as more broadly described above and in the appended claims.

EXAMPLE 1

A. Twenty-three 4×5 inch* swatches of a closed pore non-retriculated microsponge having a 1/16 inch thickness and about 70 pores/inch were soaked to saturation in a bath of 25/8 fluid ounces of hair reducing lotion having the following formulation:

*Generally, swatches of 4×3-6 inches are employed, depending upon the length of the winding rod.

| Ingredients (System pH 9.2–L 9.3) | Parts by Weight |
|---|---|
| Ammonium thioglycolate, 60% | 8.50 |
| Ammonium hydroxide, 26% | 0.82 |
| Monoethanolamine | 2.46 |
| Clouding agent | 1.00 |
| Perfume | 0.75 |
| Non-ionic surfactant (CO-630) | 0.50 |
| Deionized water QS to | 100 |

The swatches were gently squeezed until no dripping occurred and the microsponge contained about 20 grams of reducing lotion per square meter. Alternatively, the swatches can be partially dried in an air oven at about 30° C. for about 0.5 to about 3 hours. The damp swatches containing about 5 times their weight of reducing liquid were then sealed in a plastic container for future use.

B. After 10 days, the swatches prepared in the above manner were employed in permanent waving to the hair of a test subject.

The hair of the subject was moistened with warm water and divided into 23 sections from the crown of the scalp to ear lobe. The hair of each section was combed straight, wrapped in one of the moist swatches and wound on a curling rod having a 3/8 inch diameter and about 5 inch length. The entire wrapping with hair reducing application was completed in 8 minutes. A plastic cap was then placed over the rolled area and the subject placed under a drier at medium heat for 5 minutes to complete the reducing process, after which the hair on curling rods was thoroughly rinsed with water, during which time the wrappers were squeezed to assist rinsing. The hair was then blotted with an absorbent towel to eliminate dripping and then 4 fluid ounces of neutralizer having the following formulation was uniformly poured over the wrapped hair.

| Ingredients | Parts by Weight |
|---|---|
| Hydrogen peroxide, 35% | 5.00 |
| Isostearamidopropyl morpholine lactate | 0.75 |
| Cetearyl alcohol | 0.50 |
| Mineral oil | 0.07 |
| Methyl parahydroxybenzoate | 0.10 |
| Phenacetin | 0.10 |
| Citric acid | 4.00 |
| N—dodecyl-2-pyrrolidone | 3.00 |
| Fragrance | 0.50 |
| Deionized water | QS |
| Sodium nitrate to pH | 1.9 |

The neutralizing solution was allowed to remain on the wrapped hair for 8 minutes during which time the solution was taken up and uniformly applied by the porous wrappings so that dripping was minimized. After neutralization the hair was again rinsed and brush blow dried.

The entire permanent hair waving operation was completed in about 25 minutes. The permed hair had a silky, soft texture and tight uniform curls with no crimped or burnt ends. No hair breakage, frizzing or snarling occurred during shaping and brushing.

EXAMPLE 2

A second test subject was tested with Zotos Design Freedom permanent waving lotion (5 fluid ounces) using sponge swatches and the procedure described in Example 1 for impregnation. The hair of test subject was not previously processed, had a fine texture, good condition and was neither dry nor oily.

In the present treatment, the hair was sectioned into 25 parts and the distal ends of each part was wrapped in an impregnated sponge swatch end paper and rolled on a permanent hair setting rod of about ¼ inch diameter and 5 inch length, top of the earlobe and proceeding to the top crown area and front of both sides. The entire scalp and rolled rods were then misted by uniformly spraying with deionized water from a spray bottle. A plastic cap was then placed over the subject's scalp and processing with the reducing lotion was allowed to take place for a period of 10 minutes, after which the rolled hair was thoroughly rinsed with water, blotted and 3 fluid ounces of neutralizing solution uniformly applied to saturate the wrapped hair. The neutralizing solution had the following composition.

| Ingredients | Parts by Weight |
|---|---|
| Hydrogen peroxide, 35% | 4.50 |
| Citric acid | 0.20 |
| Polyoxyethylene lauryl ether | 0.50 |
| Latex opacifier | 0.10 |
| Phenacetin | 0.04 |
| Deionized water | 94.26 |
| Fragrance | 0.40 |

The neutralizing solution was allowed to remain on the hair for 3 minutes after which the rods were removed and an additional 3 fluid ounces of neutralizer was uniformly applied to the unwrapped curls. After 2 minutes, the hair was rinsed thoroughly with lukewarm water, toweled to remove excess moisture and the hair was then brushed dried.

A third test subject having the same hair characteristics as the second test subject was selected for a permanent hair curling. According to normal procedure, the subject's hair and scalp were thoroughly saturated with water and allowed to drip dry. The hair was sectioned into 25 sections and the distal ends of each section were wrapped in conventional non-impregnated paper as described above and then rolled on the identical size permanent hair setting rods. The subject was then placed in a reclining position while the reducing solution described above (5 fluid ounces) was poured over the hair wrapped on rods. It was necessary to place a strip of absorbent cotton round the entire hair line of the subject to absorb excess lotion draining from the rods, after which the subject was placed in an upright position. It was also necesssary to place a towel around the neck and shoulders of subject to absorb a major portion of the liquid run-off. Significantly more reducing lotion was needed in this operation to assure uniform and continued saturation of the hair sections. The reducing lotion was allowed to remain on the hair for a period of 10 minutes, during which drying portions of the rolled hair were remoistened with reducer lotion. The rolled hair was then thoroughly rinsed with water and neutralized for 3 minutes with 6 fluid ounces of the above described neutralizing solution. The rods were then removed and the hair rerinsed with lukewarm water, toweled and brushed dried.

A comparison between the process of the present invention employing the impregnated wrappers and that of a conventional hair perm process employing non-impregnated wrappers is shown in the following Table.

TABLE

| Evaluation | Process Using Impregnated Wrappers | Process Using Non-impregnated Wrappers |
|---|---|---|
| A. Reducing Lotion | | |
| test curl | good | fair |
| scalp redening | none | some |
| processing time | 10 min. | 10 min. |
| penetration | good | good |
| time of application, for rolling and reducer application | 2 min. | 5 min. |
| B. Neutralization | | |
| Penetration | good | good |
| Pick-Up | more uniform faster acting | fair |
| Scalp Sensation | none | none |
| C. Hair Characteristics | | |
| Frizz | none | some |
| Breakage | none | some |
| Curl | tight | more relaxed |
| Springiness | excellent | fair |
| Luster | excellent | good |
| Feel | soft | soft |
| Scalp & skin irritation | none | slight redening |
| Operator preference | x | |

The above comparative results establish that better penetration, tighter curl with less frizz is achieved with the process of the present invention employing the hair end wrappers which have been impregnated with the reducing solution.

EXAMPLE 3

As in Example 1A swatches saturated with the reducing solution are prepared and the procedure described in Example 1B is repeated except that the damp hair rolled on rods and the impregnated swatches applied over each rod after rolling. Allowing the reducing solution to penetrate the hair from that portion nearest the scalp to the distal ends next to the rod surface. This procedure provides a tighter curl to the hair next to the scalp and may reduce frizzing of ends since, by allowing the reducing solution to penetrate from exposed rolled portions to the inner distal ends, the ends may not receive the same amount of saturation during the entire processing period. However, this procedure is more time consuming and therefore is not preferred.

EXAMPLE 4

As in Exmaple 1A swatches saturated with a viscous reducing lotion having the following composition are prepared.

| Ingredients | % by Weight |
|---|---|
| Emulsifying wax NF (Polawax) | 7.5 |
| Cetyl alcohol (Crodacol C-95) | 1.0 |
| Petrolatum (Protopet) | 4.0 |
| Carnation mineral oil | 15.0 |
| Steareth 2 (Volpo S-2) | 0.5 |
| DEA-oleth-10 phosphate (Crodafos N10N) | 1.5 |
| Propylene glycol | 2.0 |
| Steareth 10 (Volpo S-10) | 2.5 |
| Deionized water | 53.0 |
| NaOH, 25% | 12.0 |

-continued

| Ingredients | % by Weight |
|---|---|
| Diazolidinyl urea (and) methylparaben (and) propylparaben (and) propylene glycol (Germaben II) | 1.0 |

The procedure of Example 1B is then repeated except that rods of 5-6 inches are employed to replace the smaller curling rods. The hair condition resulting from this straightening procedure is similar to that of Example 1.

Other absorbent materials described in the foregoing discussion can be substituted in any of the preceding examples for impregnation with conventional reducing lotions or lotions which are optionally promoted with a quaternized or non-quaternized lactam. Also, any of the conventional employed permanent waving or permanent hair straightening lotions can be substituted for Zotos Design Freedom hair permanent lotion employed in Example 2. Such conventional hair altering lotions include any of those also described in co-pending patent applications Ser. Nos. 13,617 and 60,285 (supra). Similarly, other neutralizing lotions, including those described in Ser. Nos. 13,617 and 60,285 (supra) can be substituted in the above examples.

What is claimed is:

1. An article of manufacture adapted for permanently altering the structure of hair which comprises a flexible hair wrapping material capable of absorbing and retaining between about 5 and about 15 times its weight of water and a water soluble hair reducing lotion containing between about 0.01 weight % and about 7 weight % of an N—$C_8$ to $C_{22}$ alkyl lactam conditioner, which lotion is impregnated or coated on said wrapping in an amount of between about 3 and about 130 grams/square meter of wrapping.

2. The article of claim 1 wherein the wrapping is sponge having a thickness of from about 1/32 to about 1 inch thickness and having from about 5 to about 150 pores/inch.

3. The article of claim 1 wherein the wrapping is an absorbent paper.

4. The article of claim 1 wherein the wrapping is a closed pore non-reticulated microsponge.

5. The aritcle of claim 4 wherein the microsponge is in the form of a swatch or pad having a dimension of about 4×3-6 inches and between about 40 and about 120 pores/inch.

6. The article of claim 5 wherein the swatch has a thickness of from about 1/32 to about ¼ inch.

7. The article of claim 1 wherein the wrapping is in the form of a winding rod on which the hair is wound.

8. The article of claim 1 wherein the hair reducing lotion is impregnated or coated on said wrapping in an amount of between about 3 and about 50 grams/square meter of wrapping.

9. The process for preparing the wrapping of claim 1 which comprises contacting the wrapping material with said reducing lotion for a period sufficient to permit an increase of between about 3 and about 15 times the weight of wrapping.

10. The process of claim 9 wherein said wrapping is precut to desired dimension and a plurality of said wrappings are packaged in a damp state.

11. The process of claim 9 wherein said wrapping is a microsponge having from about 5 to about 150 pores/inch.

12. An article of manufacture adapted for permanently altering the structure of hair which comprises a flexible hair wrapping material capable of absorbing and retaining between about 5 and about 15 times its weight of water and a water soluble hair reducing lotion containing between about 0.01 weight % and about 7 weight % of an N-quaternized amino lactam having the formula

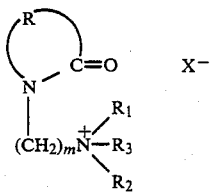

wherein m is an integer having a value of from 1 to 4; R is linear alkylene having from 3 to 8 carbon atoms and is optionally substituted with $C_1$ to $C_4$ alkyl; $R_1$, $R_2$ and $R_3$ are each independently selected from the group of alkyl, alkylneoxy, alkylhydroxy, alkoxy, aryl, aralkyl, alkaryl, and alkylene amidoalkyl radicals, said groups each having from 1 to 30 carbon atoms, and at least one of $R_1$, $R_2$ and $R_3$ is a radical having from 8 to 30 carbon atoms; and $X^-$ is a chloride, bromide or iodide anion, which lotion is impregnated or coated on said wrapping in an amount of between about 3 and about 130 grams/square meter of wrapping.

13. The article of claim 12 wherein R of the N-quaternized amino lactam is $C_3$-alkylene.

14. The article of claim 12 wherein said reducing lotion contains between about 0.5 weight % and about 5 weight % of said lactam.

15. The article of claim 12 wherein said N-quaternized amino lactam is dimethyl hexadecyl-[N-(2-pyrrolidonyl)methyl]chloride and wherein said lotion contains between about 0.75 % and about 1.5% of said lactam.

16. The article of claim 12 wherein said N-quaternized amino lactam is dimethyl octadecyl-[N-(2-pyrrolidonyl)methyl]chloride and wherein the lotion contains between about 0.75 % and about 1.5% of said lactam.

17. The article of claim 12 wherein said flexible hair wrapping material is a sponge having a thickness of from about 1/32 to about 1 inch.

* * * * *